US012412662B2

(12) United States Patent
Fahner et al.

(10) Patent No.: US 12,412,662 B2
(45) Date of Patent: Sep. 9, 2025

(54) SUPERVISED MACHINE LEARNING-BASED MODELING OF SENSITIVITIES TO POTENTIAL DISRUPTIONS

(71) Applicant: FAIR ISAAC CORPORATION, Minneapolis, MN (US)

(72) Inventors: Gerald Fahner, Austin, TX (US); Brad Vancho, San Francisco, CA (US)

(73) Assignee: FAIR ISAAC CORPORATION, Minneapolis, MN (US)

( * ) Notice: Subject to any disclaimer, the term of this patent is extended or adjusted under 35 U.S.C. 154(b) by 0 days.

(21) Appl. No.: 18/367,849

(22) Filed: Sep. 13, 2023

(65) Prior Publication Data

US 2024/0013919 A1      Jan. 11, 2024

Related U.S. Application Data

(63) Continuation of application No. 17/469,794, filed on Sep. 8, 2021, now Pat. No. 11,804,302, which is a continuation-in-part of application No. 15/801,265, filed on Nov. 1, 2017, now abandoned.

(51) Int. Cl.
| | |
|---|---|
| G06Q 10/06 | (2023.01) |
| G06N 20/20 | (2019.01) |
| G06Q 10/0635 | (2023.01) |
| G06Q 10/0637 | (2023.01) |
| G06Q 30/02 | (2023.01) |
| G06Q 40/03 | (2023.01) |
| G16H 50/20 | (2018.01) |
| G16H 50/30 | (2018.01) |

(52) U.S. Cl.
CPC ............ G16H 50/20 (2018.01); G06N 20/20 (2019.01); G06Q 10/0635 (2013.01); G06Q 10/06375 (2013.01); G06Q 40/03 (2023.01); G16H 50/30 (2018.01)

(58) Field of Classification Search
CPC .............................. G06Q 10/06; G06Q 30/02
USPC ........................................................ 705/7.28
See application file for complete search history.

(56) References Cited

U.S. PATENT DOCUMENTS

| | | |
|---|---|---|
| 7,840,484 B2 | 11/2010 | Haggerty et al. |
| 8,504,456 B2 | 8/2013 | Griffin et al. |
| 8,515,862 B2 | 8/2013 | Zhang et al. |

(Continued)

OTHER PUBLICATIONS

Fahner, G. "Estimating causal effects of credit decisions." *International Journal of Forecasting*, 28 (2012), Issue 1, Jan.-Mar. 2012, 248-260.

(Continued)

*Primary Examiner* — Nga B Nguyen
(74) *Attorney, Agent, or Firm* — Mintz, Levin, Cohn, Ferris, Glovsky and Popeo, P.C.; F. Jason Far-hadian, Esq.

(57) ABSTRACT

Computer-implemented systems, methods and products for modeling sensitivities to potential disruptions by observing performances of entities in a first sub-population and a second sub-population using a machine learning model comprising a set of predictors and a binary indicator variable associated with a first entity subjected to a first event associated with the first sub-population, the machine learning model trained to predict an expected performance for the first entity based on at least one of a known attribute associated with the first entity in relation to the first event and a value of the binary indicator variable associated with the first event.

20 Claims, 12 Drawing Sheets

(56) References Cited

U.S. PATENT DOCUMENTS

| | | |
|---|---|---|
| 11,804,302 B2 * | 10/2023 | Fahner .................. G06Q 10/04 |
| 2005/0234688 A1 | 10/2005 | Pinto et al. |
| 2009/0037308 A1 | 2/2009 | Feinstein |
| 2011/0078073 A1 | 3/2011 | Annappindi |
| 2012/0246048 A1 | 9/2012 | Cohen et al. |
| 2013/0268468 A1 | 10/2013 | Vijayaraghavan et al. |
| 2017/0316511 A1 * | 11/2017 | Chang .................... G06Q 40/12 |
| 2019/0130481 A1 | 5/2019 | Fahner et al. |
| 2019/0325354 A1 * | 10/2019 | Rajnayak ............ G06F 18/2413 |
| 2021/0142910 A1 | 5/2021 | Hafez et al. |
| 2021/0241923 A1 * | 8/2021 | Foschini ................ G16H 40/20 |
| 2021/0264466 A1 | 8/2021 | Aggarwal et al. |
| 2021/0374033 A1 | 12/2021 | Yang et al. |
| 2022/0028561 A1 | 1/2022 | Klasson |

OTHER PUBLICATIONS

Friedman, J.H. (Feb. 28, 2002, e-published Jan. 30, 2002). "Stochastic Gradient Boosting." Computational Statistics and Data Analysis, 38(4):pp. 367-378.

Rosenbaum, P.R. and Rubin, D.B. "The Central Role of the Propensity Score in Observational Studies for Causal Effects." Biometrika (1983), 70, (1), pp. 41-55.

\* cited by examiner

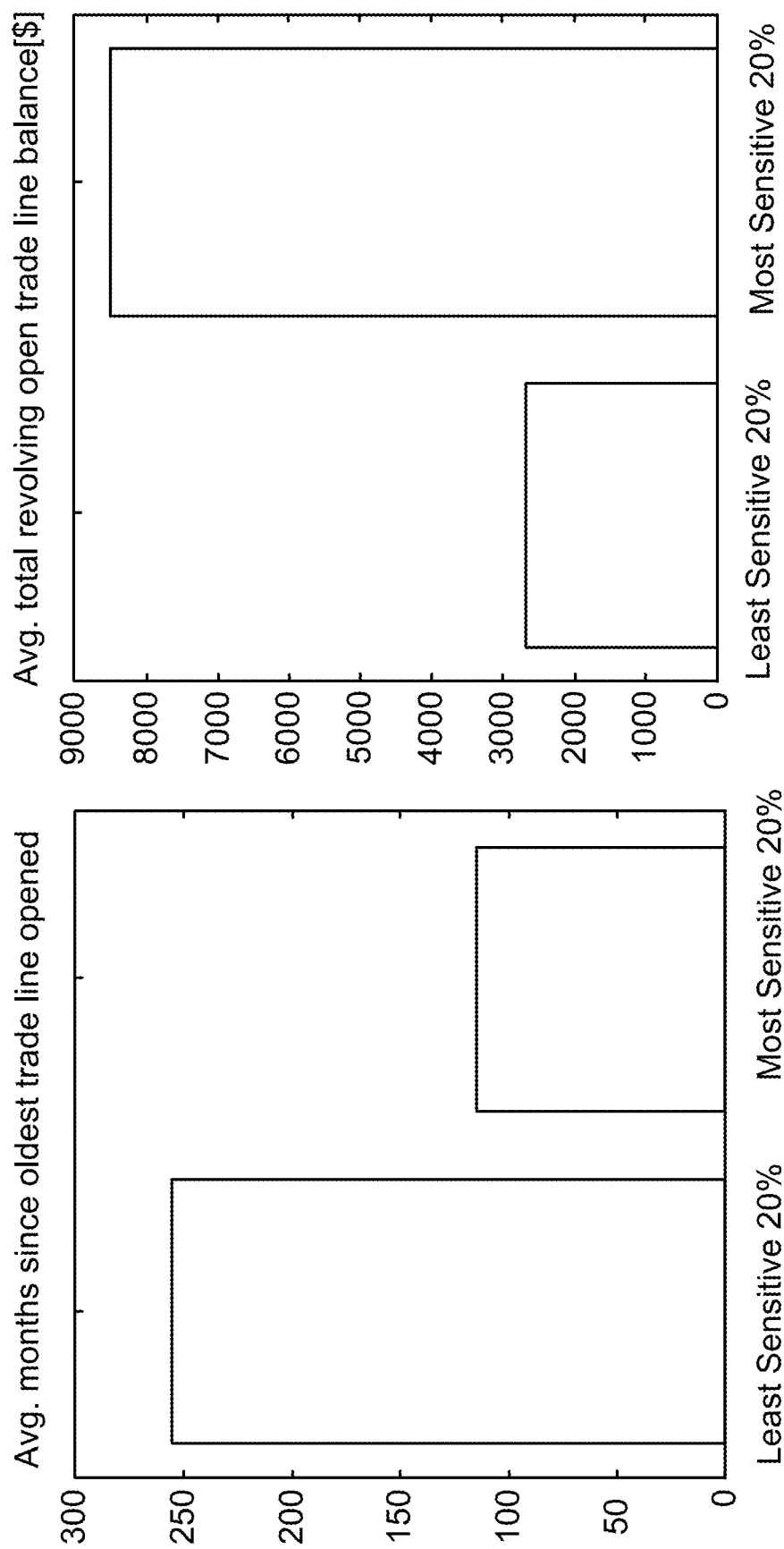

SUPERVISED MACHINE LEARNING-BASED MODELING OF SENSITIVITIES TO POTENTIAL DISRUPTIONS

CROSS REFERENCE TO RELATED APPLICATIONS

This application is a continuation of and claims priority to the earlier filing date of U.S. patent application Ser. No. 17/469,794, filed on Sep. 8, 2021, which is a continuation-in-part of and claims priority to the earlier filing date of U.S. patent application Ser. No. 15/801,265, filed on Nov. 1, 2017 the content of which is hereby incorporated herein in its entirety.

TECHNICAL FIELD

The subject matter described herein relates to supervised machine learning-aided analysis of historical data sets for development of models for quantifying sensitivity of outcome predictions to potential future disruptions.

BACKGROUND

Predictive modeling is broadly applicable in many industries. In particular, there is a need for robust modeling that can quantify a sensitivity of a given outcome prediction to a potential future binary disruption. For example, predictions of expected drug efficacy, resilience of a manufacturing process or an energy grid, etc. may not properly account for unknown sensitivities to occurrence of a future disruption. Currently available approaches to quantifying such sensitivities are either highly speculative or computationally unwieldy.

SUMMARY

This document presents systems, methods, and techniques for developing and using machine learning-based for use in preparing and analyzing historical data to generate models for quantifying sensitivity of predictions regarding an entity's expected performance to some future potential disruption.

In one aspect, a method of training a sensitivity index model for predicting the sensitivity of an entity to a potential future disruption includes identifying a population of entities for which historical data attributes for each of a plurality of data attributes are available contemporaneous to an event that causes a binary disruption in the status quo or contemporaneous to an absence of the event or to a less disruptive second event, and dividing the population of entities into a first sub-population and a second sup-population. The first sub-population experiences the event and the second sub-population does not experience the event or experiences the less disruptive second event. The dividing includes calculating a propensity score for the entities in the population of entities using supervised machine learning and creating pairs of matched entities in the population of entities such that the propensity score for each entity in the first sub-population is similar to that of a matched entity in the second sub-population.

The method further includes modeling observed performances of the entities in the first sub-population and the second sub-population, which includes defining a set of predictors and a binary indicator variable for each entity, and producing a model for predicting outcomes based on an entity's historical data attributes and a value of the binary indicator variable. Expected performances of the entities in both the first and second sub-populations are calculated under disrupted and less disrupted conditions using the model, which includes, for each entity, varying the value of the binary indicator variable while keeping the entity's historical attribute values fixed.

A sensitivity value is calculated for each entity by quantifying a difference between the calculated expected performance under the disrupted condition and the expected performance under the less disrupted condition, and a sensitivity index model is generated, which includes using supervised learning techniques based on the calculated sensitivity values and the historical attribute values for each entity.

In another aspect, a method for generating a sensitivity index score for an entity of interest includes receiving input attribute values of one or more of a plurality of historical data attributes for the entity of interest and using the input attribute values as model inputs to a sensitivity index model trained with a training process as described in the preceding aspect.

An improved computer-implemented machine learning system is also provided that includes one or more processors coupled to one or more data storage devices to process or store data associated with known attributes for a plurality of entities subjected to a plurality of known events. A machine learning model implemented as a data structure stored in the one or more data storage devices, the machine learning model trained to observe performances of the plurality of entities in a first sub-population and a second sub-population.

The machine learning model may be associated with a set of predictors and at least a binary indicator variable corresponding to a first entity subjected to a first event experience by members of the first sub-population. The machine learning model may be trained to predict an expected performance for the first entity based on at least one of (1) a known attribute associated with the first entity in relation to the first event and (2) a value of the binary indicator variable associated with the first event.

Members of the first sub-population and the second sup-population are distinguishable based on whether one or more events have been experienced by the members of the first sub-population and the second sup-population, the members of the first sub-population experiencing the first event and the members of the second sub-population experiencing the second event. An expected performance of the first entity subjected to the first event is determined based on a sensitivity value determined for the first entity by quantifying an expected performance of a member of the first sub-population subjected to the first event according to a sensitivity index generated based on different permutations of potential outcomes for the plurality of known events.

A treatment may be applied to the first entity, responsive to the determined expected performance. The first-subpopulation and the second sub-populations optimally capture a binary test of a type of outcome for the sensitivity index based on different events with different time periods associated with different known attributes. The different known attributes are contemporaneous to at least one of (1) the different events causing a binary disruption in the first entity's status quo, (2) an absence of the first event, and (3) the second event being less disruptive than the first event. The different known attributes may have values that are non-randomized, such that the first entity experiencing the first event and a second entity experiencing the second event exhibit materially different distributions of said values.

In one embodiment, the sensitivity index is generated based on at least a first disruption type or a first target outcome. A known attribute is determined based on historical data associated with a population of entities having been subjected to an event. The population is divided into the first sub-population and the second sub-population based on a propensity score calculated for pairs of matched entities in the population. The first event comprises a first medical treatment and the second event comprises a second medical treatment not including the first medical treatment. The historical data comprises one or more of age, weight, body mass index, ethnic background, socio-economic factors, and health condition. The sensitivity index predicts how sensitive a predicted health outcome for the first entity is depending on a potential future disruption in the first medical treatment.

Implementations of the current subject matter can include, but are not limited to, systems and methods including one or more features or performing one or more operations consistent with the descriptions herein as well as articles that comprise a tangibly embodied machine-readable medium operable to cause one or more machines (e.g., computers, etc.) to result in such features or operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more operations or provide one or more features described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 6A is a diagram illustrating a difference between an average number of months since the oldest trade line opened for the 20% most balance change sensitive and the 20% least balance change sensitive consumers within a risk score band, in accordance with aspects described herein;

FIG. 6B is a diagram illustrating a difference between an average total revolving trade line balance for the 20% most balance change sensitive and the 20% least balance change sensitive consumers within a risk score band, in accordance with aspects described herein;

When practical, similar reference numbers denote similar structures, features, or elements.

DETAILED DESCRIPTION

In certain aspects, the current subject matter relates to development and use of artificial intelligence and/or machine learning models to make predictions about directionality and magnitude of the effects of varying future conditions on one or more performance metrics of a given entity. Various currently available approaches in this field may rely upon large, randomizable data sets for an entire population. However, such approaches may be limited in their ability to make accurate predictions based on specific current conditions for a given individual entity without requiring generalizing assumptions.

A beneficial approach, aspects of which are discussed herein, makes use of historical data (e.g., historical attribute values for multiple data attributes relevant to the desired outcome prediction) in combination with machine learning-aided input data selection and recursive modeling based on historical data from two or more time periods identified as representative of differing levels of disruption or stress, as described herein. For non-randomized data such as the historical attribute values used in implementations of the current subject matter, entities in the first and second sub-populations (e.g., those entities in the first sub-population who experience a stressed or otherwise disrupted condition subsequent to some initial date or dates at which historical attribute values are available for these entities prior to the stressed or otherwise disrupted condition and those entities in the second sub-population who experience a less stressed or otherwise disrupted condition subsequent to some initial date or dates at which historical attribute values are available for these entities prior to the stressed or otherwise disrupted condition) typically exhibit materially different distributions of their attribute values.

Consistent with implementations of the current subject matter, historical data are prepared for use in model development by identifying first and second sub-populations which are "matched" in that an entity in the first sub-population has a sufficiently "similar" matched entity in the second sub-population. In this context, sufficient similarity is measured by the difference in a propensity score between two entities, one in the first sub-population and one in the second sub-population. The two sub-populations include entities whose historical data are available preceding and during time periods characterized by differing conditions. For example, the first sub-population is selected to include entities for whom historical data are available preceding, during, and/or after a disruptive or otherwise stress-inducing event, condition, etc. The second sub-population is selected to include entities for whom historical data are available preceding, during, and/or after an event, condition, etc. that is either not disruptive or otherwise stress-inducing or is at least less disruptive or otherwise stress-inducing.

Figure 1A:
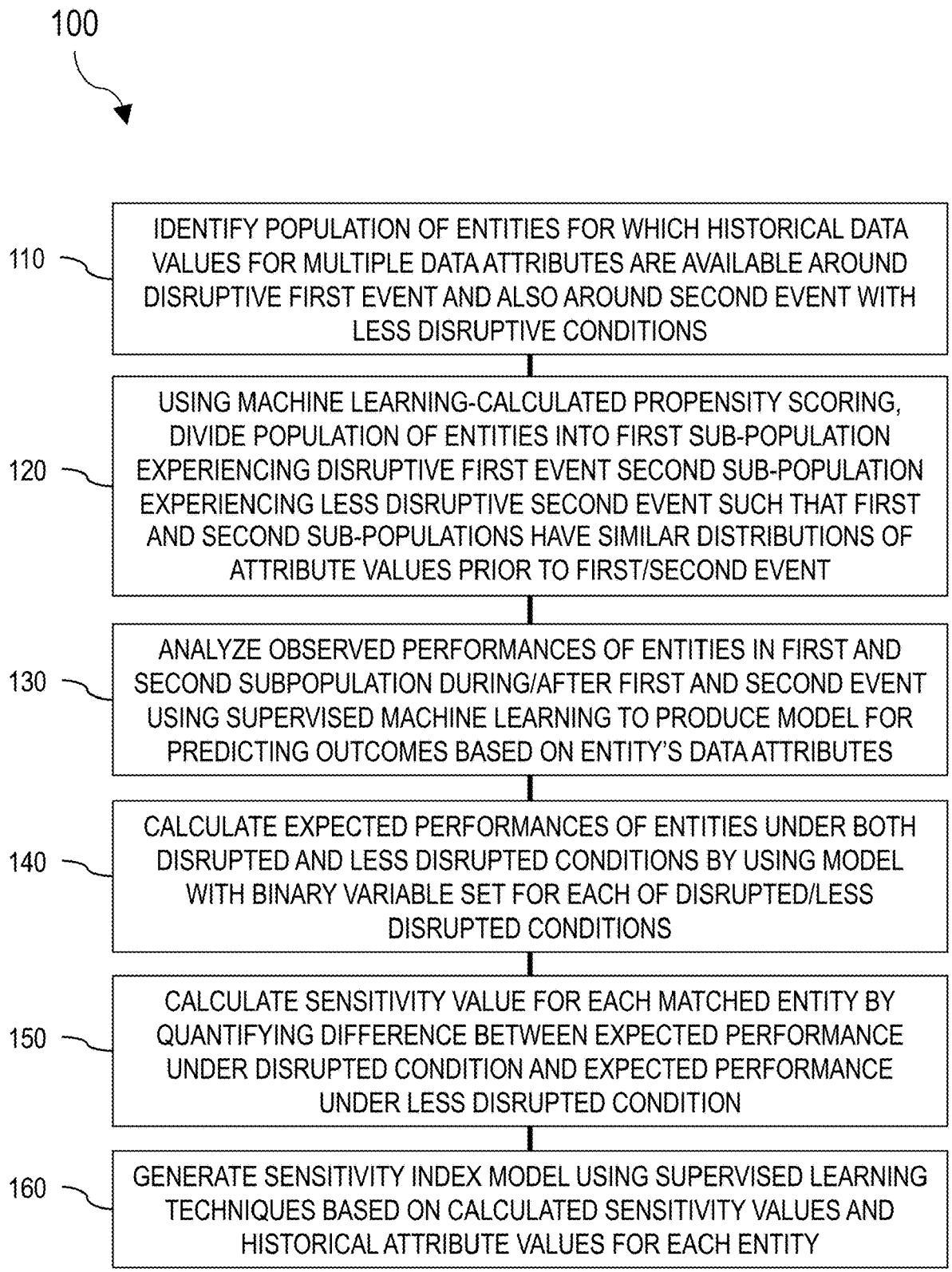
FIG. 1A is a flowchart illustrating features of a method for developing a sensitivity model, in accordance with aspects described herein.

The predictive modeling approaches described herein can be applied to a variety of predictive scenarios. As illustrated in the process flow chart shown in FIG. 1A, a model generation process includes identifying, at 110, a population of entities (e.g., devices, machines, people, companies, etc.) for which historical (e.g., time series or otherwise associated with some form of temporal information) data values for a plurality of data attributes. The available historical data values for a given entity in the population are either a) contemporaneous with (e.g., prior to and during/after) either an event, time period, etc. that causes a binary disruption that is qualitatively expected to affect a performance level, or the like of entities that experience it or b) contemporaneous with (e.g., prior to and during/after) an absence of such an event, time period, etc. For purposes of this disclosure, reference to an "event" or "time period" is intended (unless otherwise specifically narrowed) to refer to some duration of time (e.g., instantaneous or occurring of some length of time) over which some disruptive or less disruptive condition occurs for the relevant entity or entities for which historical data (e.g., historical attribute values) are available.

At 120, the population of entities is divided into a first sub-population and a second sup-population, where the first sub-population experiences an historical event or condition (also referred to as a first event in examples relating to a first event and a second event), such as for example a disruption or a period of disruption, and the second sub-population does not experience the event or condition. Alternatively, the second sub-population can experience a second event that is considered less or even non-disruptive or that otherwise serves as a "control" or baseline situation for purposes of making a binary comparison between the effects of experiencing conditions consistent with the disruptive event and the effects of not experiencing conditions consistent with the disruptive event or experiencing conditions that are not as severe as the disruptive event.

The dividing of the population of entities into the first sub-population and the second sub-population includes creating matched samples of entities from the historical data such that two sub-populations have similar distributions of attribute values at the start of the binary condition experiment. In other words, the first sub-population, which experiences a "disrupted" or "stressed" condition, and the second sub-population of entities, which experiences a "normal" or "control" condition, are chosen such that the two sub-populations are similar in their attribute distributions at or at least shortly before the time of the respective events (e.g., at the time of or at some time period before the disruptive or stressed first event or the beginning of a period of low or no disruption or stress for the first sub-population and at the time of or at some time before the non- or less-disruptive or non- or less-stressed second event for the second sub-population).

Particularly when using multivariate historical data sets with large numbers of data attributes that are not randomized and that are expected to exhibit some degree of interrelationship between values of the various attributes, selection of entities to assign to the first sub-population and the second sub-population generally requires more than merely picking two groups of entities at different times without attempting to match historical attribute values for entities from the two groups to be paired. A technical challenge in this approach is that historical data is inherently non-randomized. In a randomized experiment in which it would be possible to freely generate similar attribute distributions for randomly selected subsets of a plurality of entities such that each subset includes entities with comparable distributions of historical attribute values of a plurality of data attributes. However, for non-randomized data such as the historical attribute values used in the claimed invention, entities in the first and second sub-populations can be expected in many instances to exhibit materially different distributions of their attribute values.

While traditional statistical techniques such as discriminant analysis or logistic regression analysis can in principle be used to perform propensity score-based matching subject to their statistical assumptions (including linearity in the attributes and no interactions between the attributes, as well as absence of multicollinearities and conformity to parametric assumptions), their application can be extremely tedious. For example, to capture nonlinearities and interactions between the attributes, many transformations of the raw attributes may need to be "manually" hypothesized by an analyst and then coded and tested, and multicollinear attributes or transformations thereof may need to be detected and removed prior to inclusion into the statistical model. In such a manual process, important transformations are readily overlooked. For non-randomized data such as historical attribute values, entities in the first and second sub-populations (e.g., those entities in the first sub-population who experience a disrupted or stressed condition, such as the first event, and those entities in the second sub-population who experience a less disrupted or less stressed condition, such as the second event) may exhibit starkly different distributions of their attribute values. Conventional approaches, including use of analysts and human-guided determination of the training data, are simply not effectively applicable given the size and complexity of a large data set, for example one characterized by hundreds of data attributes, millions of entities, nonlinear and non-parametric distributions, and interactions between the attributes.

The inherent selection bias that can occur without properly preparing the input data sets may be addressed by calculating a propensity score and using a propensity score matching technique. A propensity score may be calculated for the entities in the original population using supervised machine learning. A supervised machine learning technology, such as for example that described in "Stochastic Gradient Boosting" (J. H. Friedman, Computational Statistics and Data Analysis, vol. 38, 2000, pp. 367-378) can be beneficial in developing propensity scores for the creation of the first and second sub-populations with appropriately similar data attribute value distributions. To calculate a propensity score, the supervised machine learning can be trained on a curated development data set. Such a data set can include, for each entity, a record of its attribute values and a target variable indicating the binary condition experienced by the entity (e.g. disruption on/off). After training the model, each entity can be scored based on its attribute values, resulting in a propensity score that models the likelihood that a given entity experiences the disruption.

An approach using machine learning in this manner is not limited by the abovementioned assumptions (i.e., linearity, absence of interactions, parametric distributions, absence of multicollinearities). Instead, it can address nonlinearities and interactions in a manner that human analysis cannot match and can also effectively handle nonparametric distributions and multicollinearities. The machine learning approach thus supports highly effective development of powerful propensity scores, such that propensity-score based matching may reduce or even fully remove the abovementioned selection bias.

Based on the calculated propensity scores, entities in the original population are matched using a propensity score-based matching technique. The matching provides a first sub-population of entities and a second sub-population of entities having similarly distributed values of the relevant data attributes and thereby allows reduction of selection bias effects in the modeling applied to these data sets. In some implementations of the current subject matter, a "pairwise matching algorithm" can be employed to identify pairs of entities that have very similar propensity score values (i.e. very similar likelihood of experiencing the disruption), but where one of the two entities went through the disruption and the other did not.

With the data set prepared as noted above such that the first and second sub-populations are sorted with sufficiently similar distributions of data attribute values to provide a "matched sample" of groups of entities, a set of predictors are defined. These predictors include the matched entities' historical data attributes and a binary (0/1 for "normal"/ "stressed"/disrupted) indicator variable. At 130, supervised machine learning techniques are used to model (e.g., using one or more regression techniques) the entities' observed performances based on these predictors. In other words, the current subject matter employs supervised machine learning analysis of observed performances (e.g., one or more outcomes) of the entities of the two sub-populations during and/or after the respective first and second events to produce a model for predicting outcomes based on an entity's data attributes and the event (condition) indicator.

At 140, expected performances of the entities (in both the first and second sub-populations) under normal (e.g., less disrupted) and under disrupted conditions are calculated using the models developed at 130. For each entity of the plurality of matched samples of entities, an expected performance under both of the disrupted condition and the less disrupted condition is predicted using the modeling of the observed performances. In some examples, this can be accomplished by varying the value of the binary indicator variable (e.g., predictors defined above) for an entity from 0 to 1, while keeping the entity's attribute values fixed.

At 150 a sensitivity value (e.g., Low, Medium, High) is calculated for each matched entity by quantifying a difference between the expected performance under the disrupted condition and the expected performance under the non- or less disrupted condition. In some examples, the sensitivity value can be a score derived from a difference between a first outcome score for the entity predicted at the disrupted condition a second outcome score for the entity predicted at the less-disrupted condition.

Using supervised learning techniques based on these calculated sensitivity values and the historical attribute values for each entity, at 160 a sensitivity index model is generated. The resultant sensitivity index model can be configured to produce a sensitivity index score for any entity based on input attribute values of one or more of the plurality of data attributes used in model development. The use of supervised machine learning enables accounting for the nonlinearities and non-randomized distributions of the input data. This model allows, among other potential benefits, robust predictions of an entity's sensitivity to disruptions based on their current attribute values as inputs.

Additional benefits that may be realized from some implementations of the current subject matter include the improved "explainability" of sensitivity predictions generated by the model. In certain applications, the ability to explain the sensitivity index values to users of a model, to affected entities, etc. can be quite important. Explainability may also facilitate engineering a model to be palatable to users, legally compliant, and more robust (e.g. by enforcing one or more regulations relating to the model predictions, embedding contextual knowledge, or mitigating potential data biases).

Figure 1B:
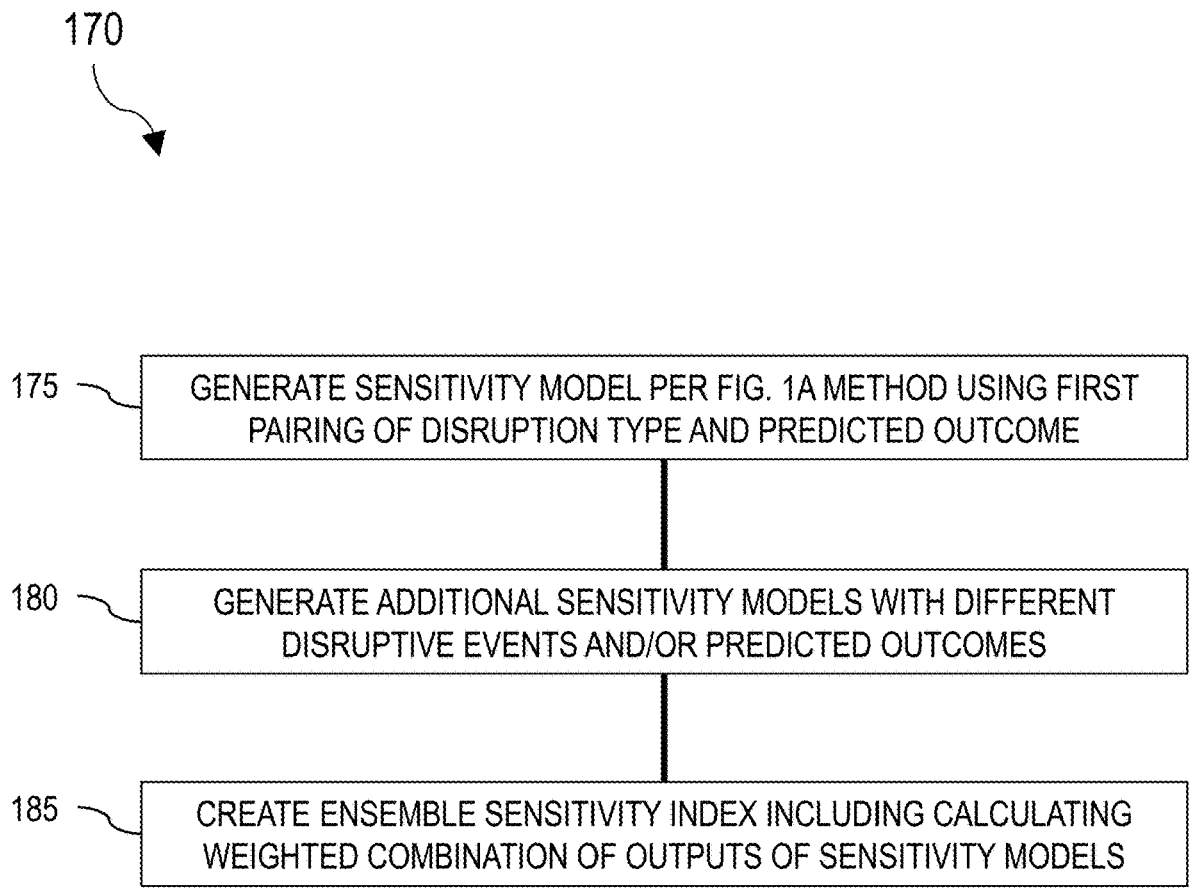
FIG. 1B is a flowchart illustrating features of a method for developing an ensemble sensitivity model, in accordance with aspects described herein.

In further aspects of the current subject matter, ensemble modeling techniques can be applied. In this context, multiple sensitivity index models are generated, where each model is based on different permutations of potential outcomes, disruptive events, etc. FIG. 1B shows a flow chart 170 illustrating certain features consistent with this aspect of the subject matter. At 175, a sensitivity model is generated per the discussion above in relation to FIG. 1A. This first model is based on a first disruption type and/or a first target outcome. At 180, a plurality of additional models are generated per the discussion above in relation to FIG. 1A. These additional models are each based on one or more different disruption types and/or target outcomes, with the operations of FIG. 1A modified accordingly. For example, selection of the first and second sub-populations can be tailored for each additional model to optimally capture a binary test of a type of disruption or outcome. This can involve using different events, with different time periods and therefore different historical data attributes associated therewith, as well as changing one or more features of the predicted outcome(s) for the entities being tested. At 185, an ensemble sensitivity index is created, where the creating includes calculating a weighted combination of the outputs of the sensitivity models. The weighted combination can involve optimizing based on analyzing the utility of each weighting for a decision maker, to provide the best possible predictions. Segmenting the outcomes in a manner consistent with this approach allows for a more focused and explainable/understandable sensitivity score, at least because the underlying models in the ensemble can be more tightly focused on types of disruption and/or predicted outcomes, such that the binary disrupted/non disrupted analysis can effectively incorporate different levels and types of disruptions and importance, relevance, etc. of predicted outcomes.

Figure 2:
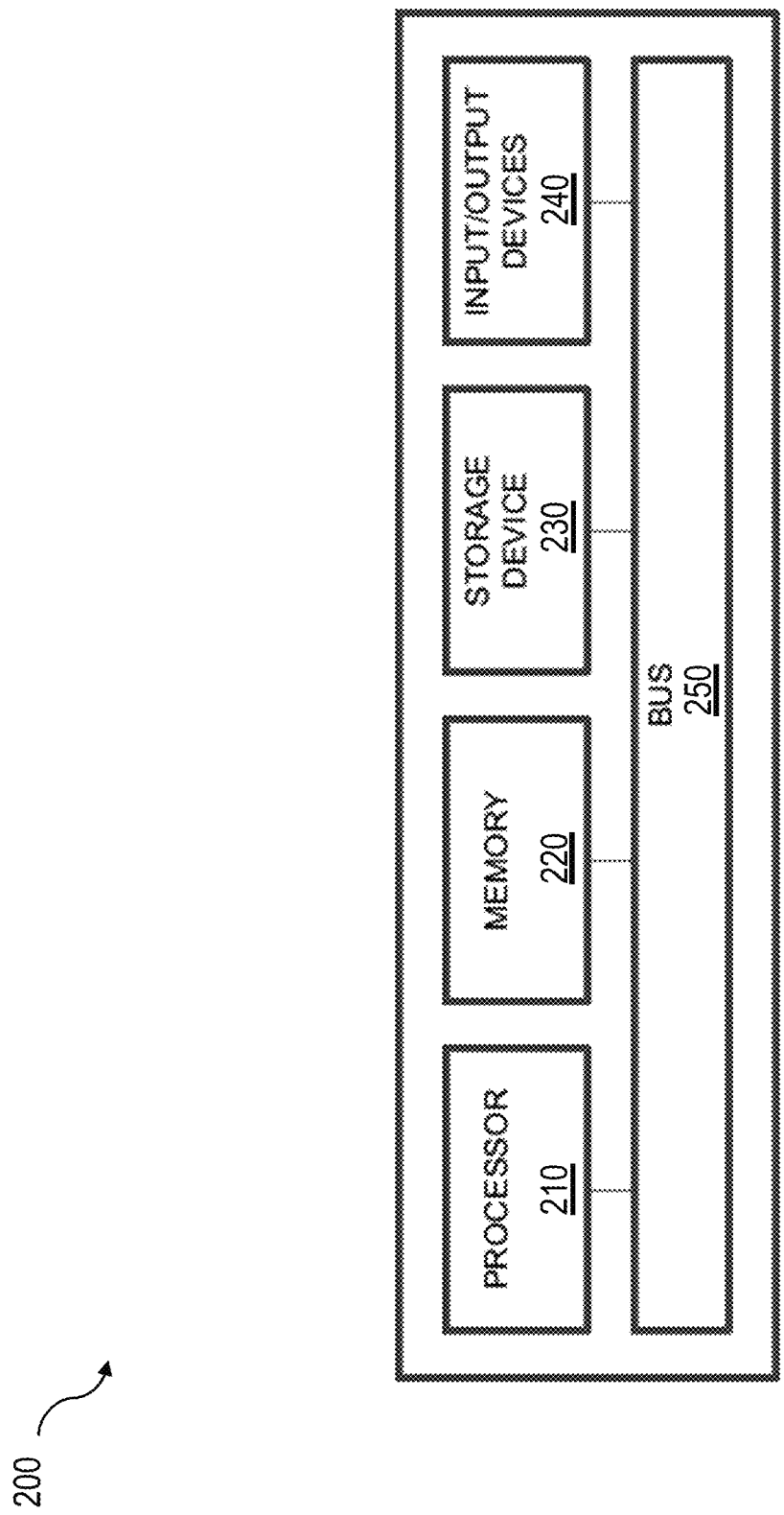
FIG. 2 depicts a block diagram illustrating a computing system, in accordance with aspects described herein.

FIG. 2 depicts a block diagram illustrating a computing system 1400, in accordance with some example embodiments. As shown in FIG. 2, the computing system 200 can include a processor 210, a memory 220, a storage device 230, and input/output devices 240. The processor 210, the memory 220, the storage device 230, and the input/output devices 240 can be interconnected via a system bus 1450. The processor 210 is capable of processing instructions for execution within the computing system 200. In some implementations of the current subject matter, the processor 210 can be a single-threaded processor. Alternately, the processor 210 can be a multi-threaded processor. The processor 210 is capable of processing instructions stored in the memory 220 and/or on the storage device 230 to display graphical information for a user interface provided via the input/output device 240.

The memory 220 is a computer readable medium such as volatile or non-volatile random-access memory (RAM) that stores information within the computing system 200. The storage device 230 is capable of providing persistent storage for the computing system 200. The storage device 230 can be a floppy disk device, a hard disk device, an optical disk device, or a tape device, or other suitable persistent storage means. The input/output device 240 provides input/output operations for the computing system 200. In some implementations of the current subject matter, the input/output device 240 includes a keyboard and/or pointing device. In various implementations, the input/output device 240 includes a display unit for displaying graphical user interfaces.

According to some implementations of the current subject matter, the input/output device 240 can provide input/output operations for a network device. For example, the input/output device 240 can include Ethernet ports or other networking ports to communicate with one or more wired and/or wireless networks (e.g., a local area network (LAN), a wide area network (WAN), the Internet).

In some implementations of the current subject matter, the computing system 200 can be used to execute various interactive computer software applications that can be used for organization, analysis and/or storage of data in various formats. The computing system 200 can be configured to run one or more supervised machine learning algorithms consistent with the features described herein. Alternatively, the computing system 200 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 240. The user interface can be generated and presented to a user by the computing system 200 (e.g., on a computer screen monitor, etc.).

The following examples are provided for context and to assist in better understanding the current subject matter. They are not intended to be limiting unless features described are incorporated into the claims which follow this description.

In one example implementation of various features of the current subject matter relates to assessment of the sensitivity of predictions of drug efficacy to potential future disruptions a patient's health, such as for example significant lifestyle changes, other health problems, disruptions in drug availability, etc. For illustrative purposes, this example relates to a cholesterol-control drug, but it will be understood that a variety of medical outcomes can be similarly modeled.

As an initial aspect of a method for training a sensitivity prediction model, historical health attribute data for a large population of subjects is processed. For the purposes of this example, the subjects (e.g., entities) can be pre-selected as a group having high cholesterol values. The population is further sorted into two sub-populations having experienced two different arms of a constructed historical experiment. For example, the first sub-population may have used cholesterol medication for some period of time prior to ceasing use of the medication (e.g., due to unwanted side-effects, changes to different types of treatment, loss of insurance coverage or other cost increase to the drug, etc.). A second sub-population can be selected to include individuals who did not experience any such disruption in treatment. Data attributes of interest can include a wide variety of variables, including age, weight, body mass index, ethnic background, socio-economic factors, other health conditions, other medications being taken, and many others.

The groupings of subjects to be included in each sub-population can be identified using a supervised machine learning calculation of a propensity score to determine if a sufficient number of subjects sharing same or similar historical attribute values are available for the first sub-population of entities and the second sub-population of subjects. This determining can involve calculating a propensity score and using a propensity score matching technique to identify matched samples of subjects who fit in the two respective sub-populations while overall contributing to a similar distribution of data attribute values between the two sub-populations.

Observed performances of the subjects in the first sub-population concurrent with and/or following the event based on the first historical attribute values are modeled, as are observed performances of the subjects in the second sub-population concurrent with and/or following the second event (or in general if the second event is merely an absence of the first event) based on the second historical attribute values. This modeling can make use of one or more supervised machine learning techniques.

Using the modeling of the two sub-populations based on their historical outcomes associated with their respective events, an expected outcome (e.g., performance, etc.) for each (i.e., from both sub-populations) subject is predicted under both conditions (e.g., experiencing the first event or the second event/not the first event). For each subject, a sensitivity value or score is calculated as a quantified difference between the predicted outcome, performance, etc. for that subject under each of the two modeled conditions (experiencing the first event or the second event/not the first event).

Then, the sensitivity values or scores for all of the subjects are used, along with their respective historical attribute values, for a supervised machine learning analysis that generates a sensitivity index model useful in quantifying how sensitive a predicted health outcome for a given subject, for whom his or her own historical attribute values are available, is to a potential future disruption such as the first event.

Another example implementation of various features of the current subject matter relates to analysis and segmentation of entities based on their sensitivities to certain conditions. Using the sensitivity segments, a risk scoring system can better detect high default risk entities and more accurately predict entity future behavior. In some examples, approaches consistent with this embodiment may enable calculation of economic or financial sensitivity index values for entities.

Risk scoring is widely used by banks and other financial institutions for assessing, and reporting, a measure of the creditworthiness of individuals. Often, risk scores are generated for an individual in association with assessing risk for a particular transaction, such as obtaining a mortgage or other loan, or opening up a new credit line such as applying for a credit card. To generate a risk score, a risk management reporting agency, typically at the request of a bank or financial institution, applies a modeling algorithm to the credit data associated with an individual.

Conventional techniques do not take into account how certain financial and economic disruptions may affect a consumer's future payment performance and their future risk score. That is, given a consumer's history, conventional techniques do not take into account whether a risk score may move in a positive direction or negative direction. Accordingly, what is needed is a solution that provides a way to quantifying sensitivity of a prediction associated with a current risk score to future disruptions, stressed conditions, etc. that could affect a consumer's future payment performance. Further, it can be beneficial to segment a seemingly homogenous population (e.g., a group of entities with similar conventional risk scores) into different groups to more accurately reflect their sensitivity to a future disruptive or otherwise stressed condition.

In some aspects, future substantial changes, or disruptions, to borrowers' situations following a date on which a convention risk score is calculated can have a substantial impact on payment performance that is not predicted by risk scores. As one consequence, such disruptions can lead to substantial discrepancies between predicted and actual future default odds. As another consequence, such changes can also reduce the rank ordering performance of the scores.

For example, for a given economic disruption, analysis of the resulting economic impact may indicate that actual default odds for a group of consumers in a homogeneous risk score band were substantially higher for a sub-group exposed after a scoring date to a recessionary economy, than for another sub-group exposed after the scoring date to a stable economy.

In another example, for a given disruption in financial obligations, analysis of the resulting economic impact may indicate that actual default odds for a group of consumers in a homogeneous risk score band were substantially higher for a sub-group who after a scoring date increased their credit card balances by substantial amounts (thereby increasing their financial obligations), than for another sub-group who after the scoring date did not increase their card balances by a substantial amount.

In some aspects, it may be desirable for lenders to identify those who are not in a financially robust situation if they face an unexpected, unavoidable cost for an expensive medical procedure, or another unexpected expense. There are many sources and types of disruptions that might have an impact on an entity's loan repayment behavior, including, but not limited to: interest rate shocks, changes to income or employment status, changes to social relationships, property loss, accidents, injuries and illnesses, etc. In general, it can be difficult, costly, and often quite impractical, to try to predict future disruptions with a high degree of confidence. Accordingly, it may be beneficial for a scoring system to account for future disruptions that are undetermined and unpredicted at a scoring date.

Disruption examples discussed herein relate to unfavorable changes to situations, also referred to as "stress factors." The disruptions, stress factors, etc. can apply equally to both positive or favorable disruptions (e.g. job promotion, inheritance, lottery win) as to negative or unfavorable disruptions. Typically, an entity's performance is expected to worsen if an unfavorable disruption occurs, and the opposite might be expected when a favorable disruption occurs. However, it is possible that if an unfavorable disruption occurs, some entities' payment performance may not worsen, and some may actually improve. For example, certain individuals might redouble their efforts to repay their debt when conditions worsen, while other individuals may benefit from difficult conditions due to various factors. Similarly, if a favorable disruption occurs, some entities' performance may not improve, and some may actually worsen. For example, a windfall may seduce certain individuals to live above their means and eventually experience hardships as a consequence.

Through improved modeling and analysis it is possible to gain insight into the variety of possible responses of entities to disruptions, without making assumptions regarding either directionality or magnitude of the effect of disruptions on individual entities' payment performances. Accordingly, the entity segmentation for analysis of economic sensitivity discussed herein may beneficially add flexibility and improved accuracy to current risk scoring models not previously available. The benefit occurs in at least segmenting heterogeneous entities into "sensitivity segments" based on a sensitivity to a disruption/condition to more accurately predict future payment performance. The entities in any given sensitivity segment can be similarly impacted by a certain type, or definition of, a disruption/condition.

Substantially worsening economic conditions, as exemplified by the Great Recession, and amassing debt, as exemplified by rapidly growing credit card balances, can be referred to as economic and financial stress factors. A consumer may or may not be exposed to a certain stress factor. Exposure to a stress factor may drive certain consumers to renege on their future credit obligations, whereas other consumers exposed to the same stress factor may hardly be affected. It may be beneficial to measure this effect to more accurately predict future payment performance and reflect that prediction in a risk score. In some implementations, a processor can implement a scoring system and create an ordinal scale of consumer sensitivities for each type, or definition, of a disruption or a stress factor. In some aspects, consumers can be ranked and segmented according to their sensitivities.

Any number of sensitivity segments can be generated as desired with lesser or finer granularities and possibly non-equal segment proportions. Segmentations with finer granularities can also be constructed by incorporating other variables into the segment definitions. For example a given sub-population grouped within a relatively small range of scores on a convention risk score model could be further sub-segmented into any number of sensitivity groups obtained from the distribution of sensitivities within the particular score range of interest.

Having constructed stress-sensitivity segments for various types of disruptions, entities (e.g., consumers) can be more deeply and more easily understood and managed in terms of the risks they pose to lenders, by not only taking into account their risk scores, but in addition, also calling out the extra risks due to impacts of possible future disruptions. These extra risks increase for consumers who are more sensitive to disruptions.

Knowledge of consumer sensitivities can enable lenders to take mitigating actions in order to reduce total risk, which arises in part is due to unpredicted disruptions. As an example, a lender worried about the next recession might reduce exposure to consumers with high economic sensitivities and increase exposure to consumers with low economic sensitivities. The lender might consider combinations of risk score values and sensitivity segments to create preference rankings whereby a consumer with a marginally lower conventional risk score yet a favorably low sensitivity might be preferred over a consumer with slightly higher risk score yet an unfavorably high sensitivity. Preferences might be expressed through marketing targeting, through accepting or rejecting a credit line request, through settings of loan limits, through pricing, etc.

In some aspects, it is possible to define an entity's sensitivity to a disruption or stress factor in the framework of the Rubin causal model, as the difference between potential performances for the entity when subjected to alternative situations or conditions, namely a "normal" condition and a "disrupted" or "stressed" condition. As such, an entity's sensitivity is an individual-level causal effect of a binary condition on future payment performance. In this framework, normal and stressed conditions appear as two arms of a thought experiment. In reality an entity can only travel along one arm of the experiment for which the entity's performance is then observed. Performance for the untraveled arm cannot be observed.

Figure 3:
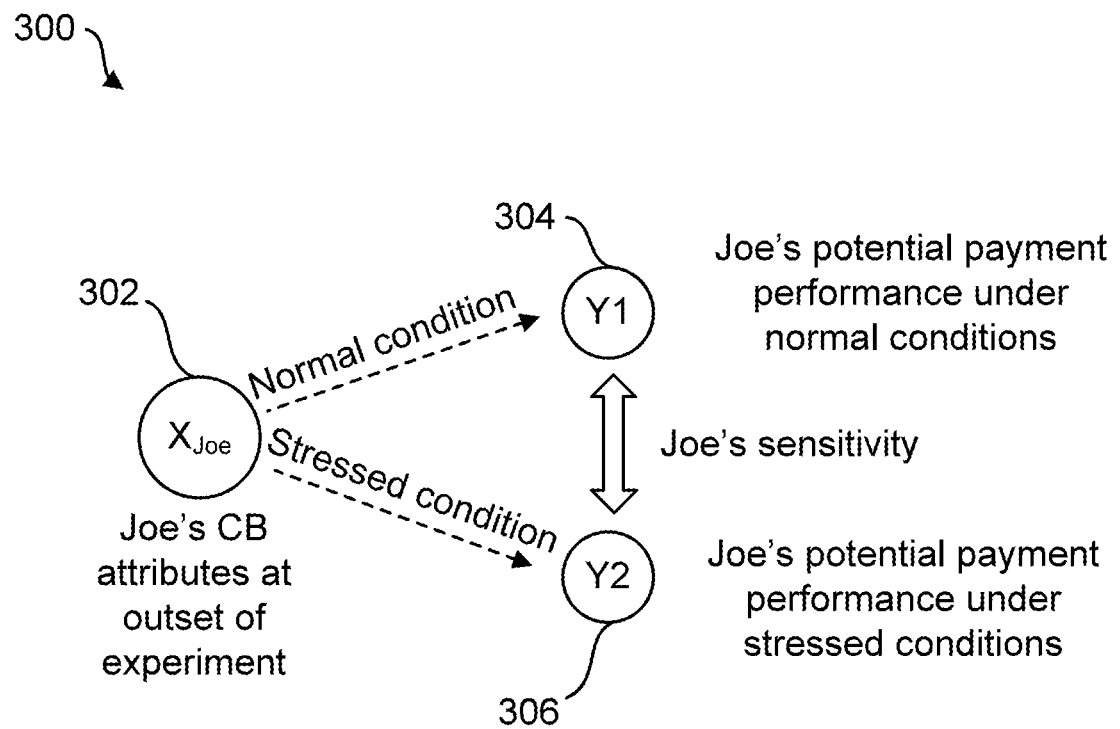
FIG. 3 is a diagram of an individual's sensitivity with respect to two different conditions (e.g., a normal and stressed condition), in accordance with aspects described herein.

FIG. 3 is a diagram 300 of an individual's sensitivity under two different conditions (e.g., a normal and stressed condition). As shown, in FIG. 3, the individual, $X_{Joe}$, 902, can have certain attribute values at the outset of an experiment, also referred to as the "scoring date." The experiment attempts to predict Joe's performance under two different conditions, a normal condition and a stressed (e.g., economic recession or downturn) condition. At the end of the experiment, the individual's (Joe's) potential performance under normal conditions is represented as Y1 904 and Joe's potential performance under stressed conditions is represented as Y2 906. Joe's sensitivity to the stressed condition (e.g., disruption or stress factor) can be defined based on the difference between Y1 904 and Y2 906.

Expanding from the example of FIG. 3, in some aspects, if certain statistical and econometric conditions hold on a sample of development data consisting of entities' attributes at a scoring date and of the experimental conditions subject to which entities' performances were observed, then it is possible to estimate individual-specific causal effects on ordinal scales. In some implementations, estimating sensitivities to financial stress factors or other disruptions as individual-specific causal effects, can leverage natural experiments in a transparent and fail-safe manner.

For example, a method of estimating individual sensitivities can include a first step of determining if there are a sufficient number of entities that share the same or similar attribute values at scoring date yet subsequently travel through different arms of the experiment. For example, if a large number of entities share one or more attribute values or similar attribute values (e.g., income, payment history, outstanding balances, number of inquiries, etc.), and those entities also experience different disruptions or stress factors (e.g., half undergo normal conditions and half undergo stressed condition). In some aspects, determining which entities share the same or similar attribute values can be based on a propensity score. In some implementations the propensity score can be calculated using any propensity score matching technique. For example, a propensity score can be calculated using a technique described in the publication "The Central Role of the Propensity Score in Observational Studies for Causal Effects" *Biometrika* 70 (1): 41-55, (1983) by Paul Rosenbaum and Donald Rubin.

If the answer is 'no' then sensitivity estimation cannot be accomplished with confidence (fail-safe). If the answer is 'yes', then a sensitivity estimating system may, in a second step, create a matched sample of entities where a first sub-population of entities travels along the normal condition arm and a second sub-population of other entities travels along the stressed condition arm, such that the two sub-populations are similar in their attribute distributions at the scoring date.

Next, in a third step, the sensitivity estimating system can define predictors comprised of the matched entities' attributes at the scoring date and a binary (0/1 for "normal"/ "stressed") indicator variable. The sensitivity estimating system can use supervised machine learning techniques to regress the entities' observed performances based on these predictors. In a fourth step, for each matched entity, the sensitivity estimating system can predict expected entities' performances under normal and under stressed conditions, by varying the value of the binary indicator variable (e.g., predictors defined in the third step) from 0 to 1, while keeping the entity's attributes fixed. Compute sensitivity value (e.g., Low, Medium, High) of each matched entity by differencing normal and stressed predictions.

In a fifth step, the sensitivity estimating system can use supervised machine learning techniques to regress the entities' sensitivity values based on the entities' observable attributes at the scoring date. For example, the regression may indicate that entities in at a certain income group have a higher sensitivity than entities in a different income group. In a sixth step, the sensitivity estimating system can use the regression model from the fifth step to predict the sensitivities of any entities of interest. The entities of interest referred to the sixth step can be new entities, such as new customers, or they can be existing entities whose attribute values may change over time, thus allowing sensitivities of entities, which need not to remain constant over time, to be regularly updated based on the latest data available on the entities. For example, a new customer can have certain attribute values that match with, or are similar to, other entities used in the sensitivity estimating system that had a Low economic sensitivity index (ESI). Accordingly, the new customer may also be assigned a Low ESI.

In some implementations, a proof-of-concept model for economic sensitivity described herein can be based on US credit bureau data collected during two starkly contrasting phases of the recent US economic cycle. Payment performance for a stable economy ("normal condition") can be collected during the 2-year window starting with scoring date October 2013 and ending October 2015. Payment performance for a recessionary economy ("stressed condition") can be collected during the 2-year window starting with scoring date October 2007 and ending October 2009 which falls into the time of the Great Recession. The binary ("normal"/"stressed") indicator was accordingly defined as: '0' for a first group of consumers whose attributes were collected in October 2013 and who subsequently performed under normal conditions; and '1' for a second group of consumers whose attributes were collected in October 2007 and who subsequently performed under stressed conditions.

In some aspects, a proof-of-concept model for credit card balance change sensitivity described herein can be based on US credit bureau data collected and combined from multiple scoring dates across a recent economic cycle, including both stable and recessionary performance periods. In this way, the balance change sensitivity model is not tied to a specific economic condition but captures averaged behaviors from across various economic conditions. Payment performance for "non-increasers" ("normal condition") was collected for consumers who didn't increase their card balances by more than $100, or decreased their card balances, over a "balance change window" of 6 months following a scoring date. Payment performance for "increasers" ("stressed condition") was collected for consumers who increased their card balances by more than $2,000 over the balance change window. In all cases, payment performance was collected over a 2-year window following the balance change window.

Figure 4:
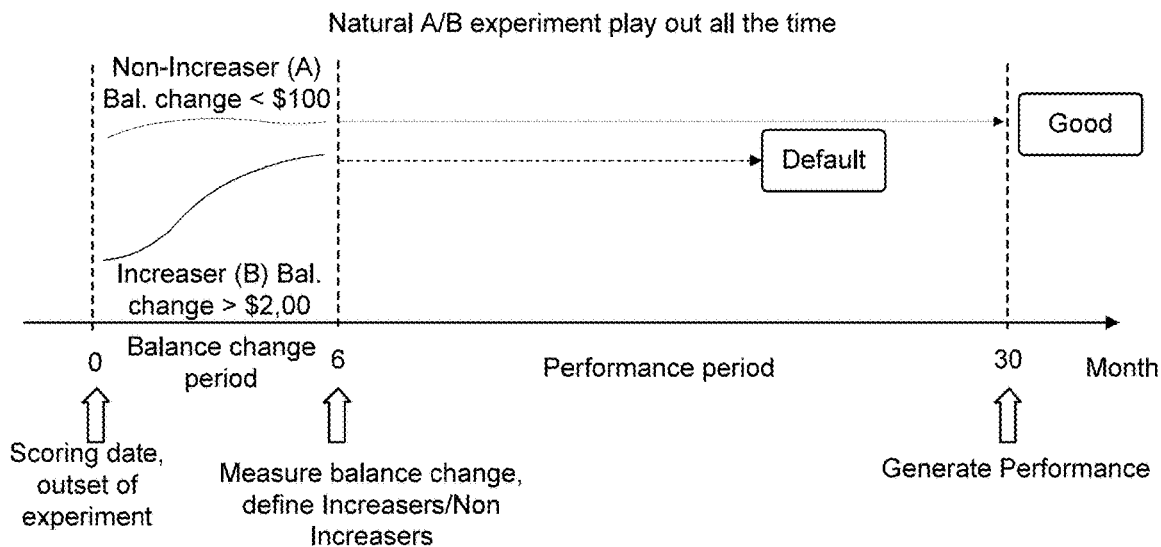
FIG. 4 is a time diagram that illustrates a longitudinal study design, in accordance with aspects described herein.

FIG. 4 is a time diagram 1000 that illustrates this longitudinal study design. The binary ("normal"/"stressed") indicator was accordingly defined as: '0' for a first group of consumers who didn't increase their card balances by more than $100, or decreased their card balances, over the balance change window, with their performances observed under these "normal" conditions; and '1' for a second group of consumers who increased their card balances by more than $2,000 over the balance change window, with their performances observed under these "stressed" conditions. As shown in FIG. 4, month 0 is the scoring date which begins the experiment. The two groups are represented as two lines, the first group is the top line 4010 and the second group is represented by the bottom line 4020. At month 6, the study can measure the credit balance change for all participants and define the two groups (e.g., define the two lines 4010 and 4020). During months 6-30 ("performance period"), the study can measure the performance of the two groups over time. At month 30, the study can perform an analysis of the two groups over the performance period and generate payment performance statistics based on the analysis.

During both model developments (e.g., economic sensitivity and balance change sensitivity) the study found sufficient numbers of entities that shared similar attribute values at the scoring date (month 0) and subsequently traveled through different arms of their experiments, (i.e. performed under "normal" and under "stressed" conditions). The study then used supervised machine learning techniques to regress the entities and calculated the economic sensitivities and the balance change sensitivities based on the entities' observable attributes at the scoring date for a large and representative sample of US consumers who regularly access consumer credit.

Figure 5A:
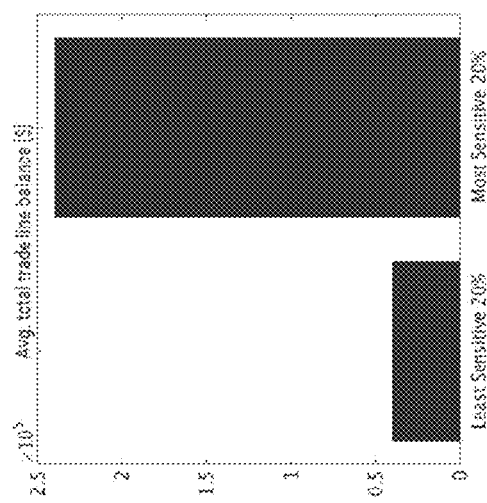
FIG. 5A is a diagram illustrating a difference between an average number of inquiries for the 20% most economic sensitive and the 20% least economic sensitive consumers within a risk score band, in accordance with aspects described herein.
Figure 5B:
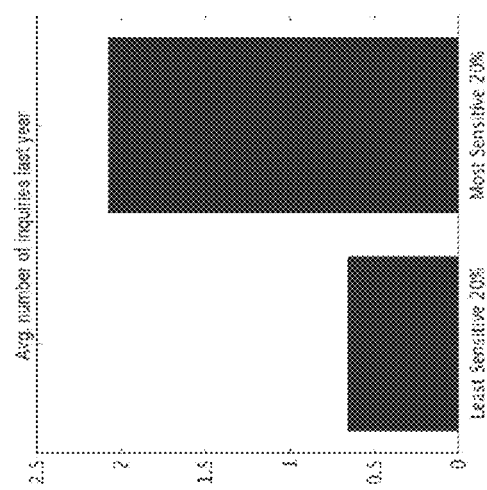
FIG. 5B is a diagram illustrating a difference between an average total trade line balance for the 20% most economic sensitive and the 20% least economic sensitive consumers within a risk score band, in accordance with aspects described herein.
Figure 5D:
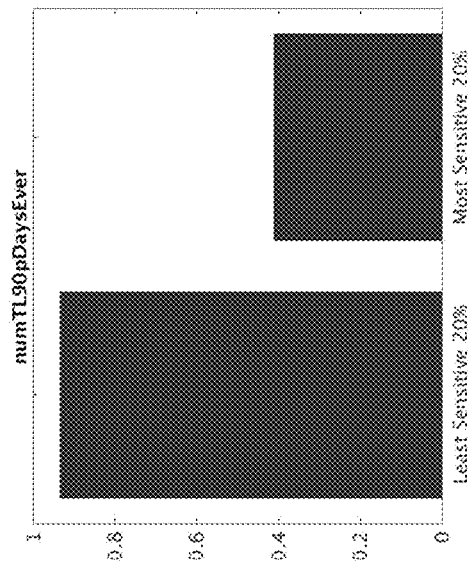
FIG. 5D is a diagram illustrating a difference between an average number of times days past due for the 20% most economic sensitive and the 20% least economic sensitive consumers within a risk score band, in accordance with aspects described herein.
Figure 5C:
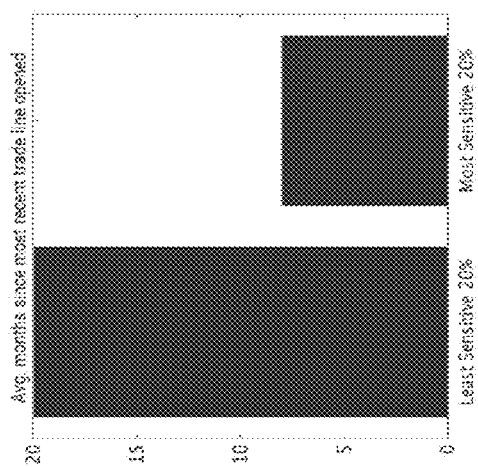
FIG. 5C is a diagram illustrating a difference between an average number of months since the most recent trade line for the 20% most economic sensitive and the 20% least economic sensitive consumers within a risk score band, in accordance with aspects described herein.

FIG. 5A is a diagram illustrating a difference between an average number of inquiries for the 20% most economic sensitive and the 20% least economic sensitive consumers within the risk score band of 678 to 682. FIG. 5B is a diagram illustrating a difference between an average total trade line balance for the 20% most economic sensitive and the 20% least economic sensitive consumers within the risk score band of 678 to 682. FIG. 5C is a diagram illustrating a difference between an average number of months since the most recent trade line for the 20% most economic sensitive and the 20% least economic sensitive consumers within the risk score band of 678 to 682. FIG. 5D is a diagram illustrating a difference between an average number of times 90 days past due for the 20% most economic sensitive and the 20% least economic sensitive consumers within a risk score band, in accordance with aspects described herein.

As shown in FIGS. 5A-D, having more credit inquiries, having higher trade line balances, having more recently a new trade line opened, and having lower average number of times days past due, are all associated with having higher economic sensitivity.

Empirically, data analysis can find that the default rate more than doubles during the stressed economic period versus the normal economic period for the 20% most sensitives in a given score band, whereas the default rate may hardly vary across economic conditions for the 20% least sensitives in this score band. Such information can be useful to companies deciding between consumers with similar risk scores but different economic sensitivity scores.

Similarly, the sub-population within the score band from 678 to 682 may be further sub-segmented, or alternatively sub-segmented, into balance change sensitivity quintiles based on the distribution of economic sensitivities within this FICO® Score band. In the illustrative example, the risk score band (e.g. from 678 to 682) is relatively narrow, such that from the traditional risk scoring perspective, this sub-population of entities would be regarded as a homogeneous risk pool. However, as illustrated below, the lowest and the highest balance change sensitivity quintile segments differ substantially in their attribute distributions.

Figures 6C, 6D:
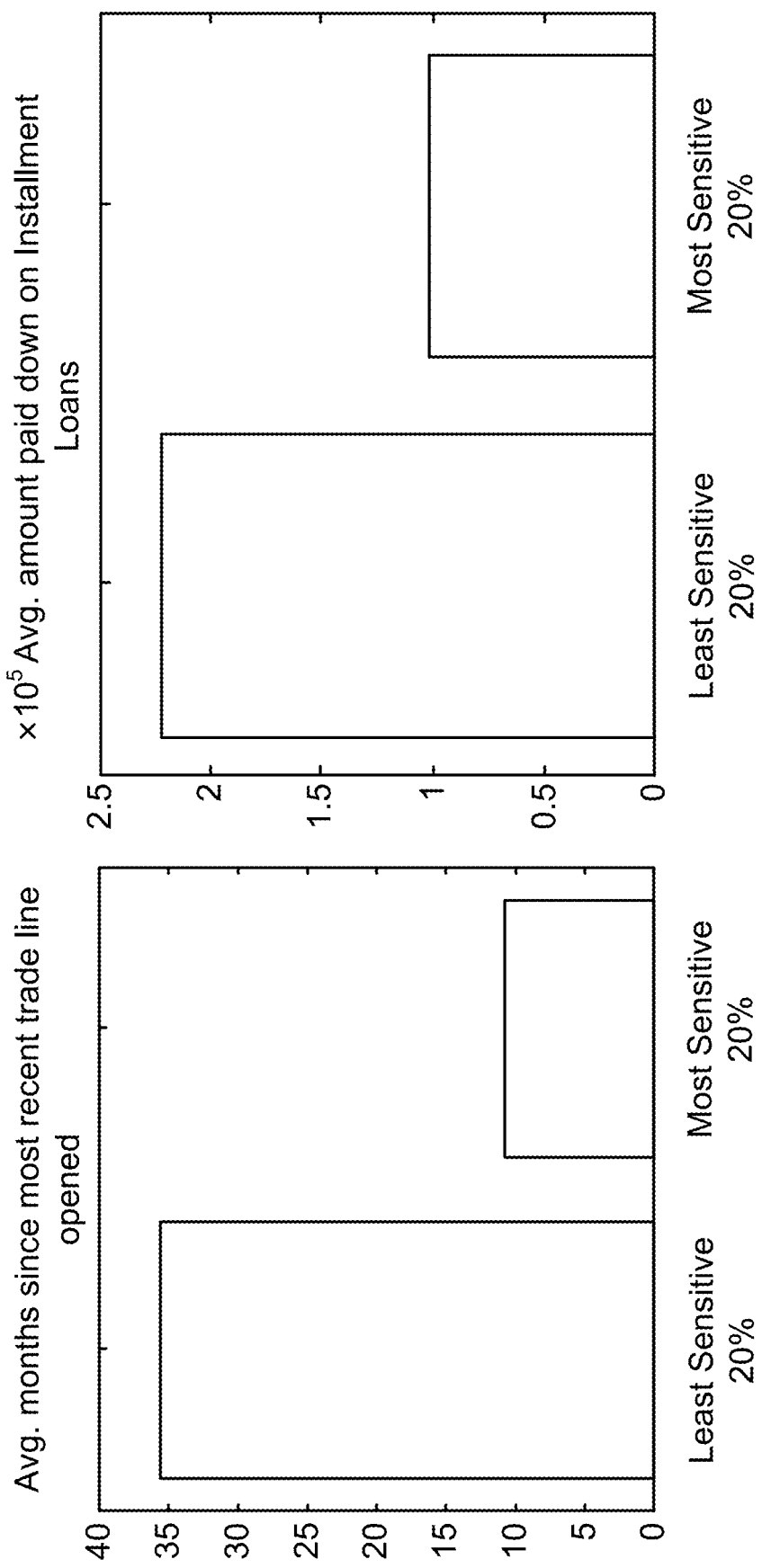
FIG. 6C is a diagram illustrating a difference between an average number of months since the most recent trade line for the 20% most balance change sensitive and the 20% least balance change sensitive consumers within a risk score band, in accordance with aspects described herein.
FIG. 6D is a diagram illustrating a difference between an average amount paid down on installment loans for the 20% most balance change sensitive and the 20% least balance change sensitive consumers within a risk score band, in accordance with aspects described herein.
Figure 6E:
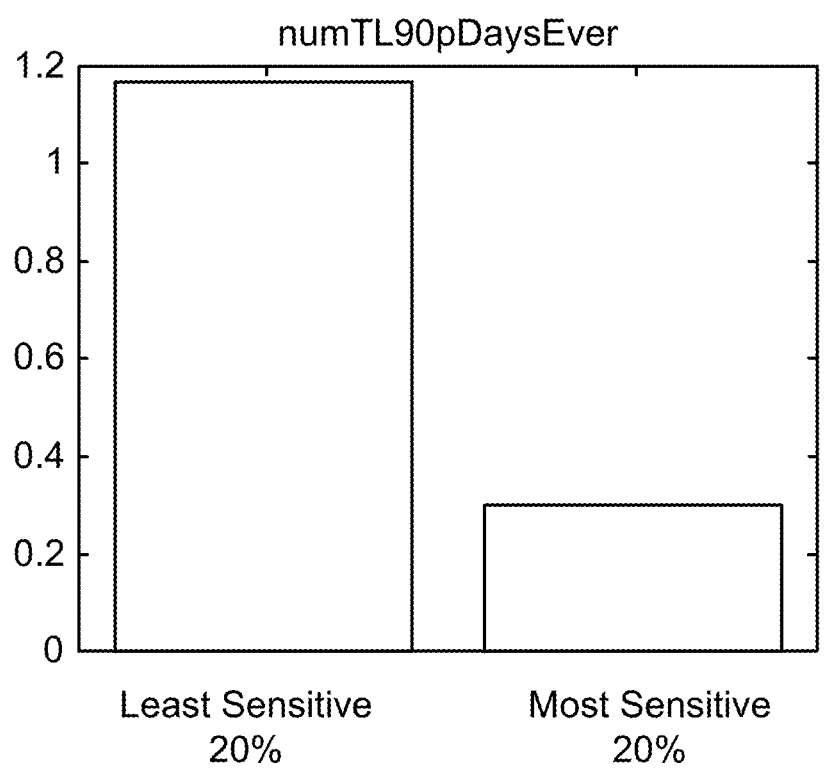
FIG. 6E is a diagram illustrating a difference between an average number of times 90 days past due for the 20% most balance change sensitive and the 20% least economic sensitive consumers within a risk score band, in accordance with aspects described herein.

FIG. 6A is a diagram illustrating a difference between an average number of months since the oldest trade line opened for the 20% most balance change sensitive and the 20% least balance change sensitive consumers within the risk score band of 678 to 682. FIG. 12B is a diagram illustrating a difference between an average total revolving trade line balance for the 20% most balance change sensitive and the 20% least balance change sensitive consumers within the risk score band of 678 to 682. FIG. 6C is a diagram illustrating a difference between an average number of months since the most recent trade line for the 20% most balance change sensitive and the 20% least balance change sensitive consumers within the risk score band of 678 to 682. FIG. 12D is a diagram illustrating a difference between an average amount paid down on installment loans for the 20% most balance change sensitive and the 20% least balance change sensitive consumers within the risk score band of 678 to 682. FIG. 6E is a diagram illustrating a difference between an average number of times 90 days past due for the 20% most balance change sensitive and the 20% least balance change sensitive consumers within the risk score band of 678 to 682.

As shown in FIGS. 6A-E, having less maturation time of oldest credit line, having higher revolving balances, having more recently a new trade line opened, having made lower down payments on installment loans, and having lower average number of times 90 days past due, are all associated with having higher balance change sensitivity.

Empirically, data analysis can find that the default rate varies considerably more across balance stress conditions for the 20% most balance change sensitive consumers than for the 20% least balance change sensitive consumers in a given score band. Such information can be useful to companies deciding between consumers with similar risk scores but different balance change sensitivity scores.

While economic and balance change sensitivities are described herein, it is possible to calculate other consumer sensitivities. For example, sensitivity scores can reflect the interplay between predictions of any kinds of behaviors of entities (not necessarily their future payment performance, and predictions not necessarily based on credit bureau data), disruptions of any kind (as long as data on the disruptions are collected), and entities' actual future behaviors. In some aspects, consumers could be segmented into groups that differ in terms of impact of health insurance loss on future investment decisions, or groups that differ in terms of impact of adopting a cholesterol-lowering medication on future levels thereof (as discussed above in the earlier example implementation), or groups that differ in terms of impact of enrollment in a driver education program on future driving skills, etc.

Figure 7:
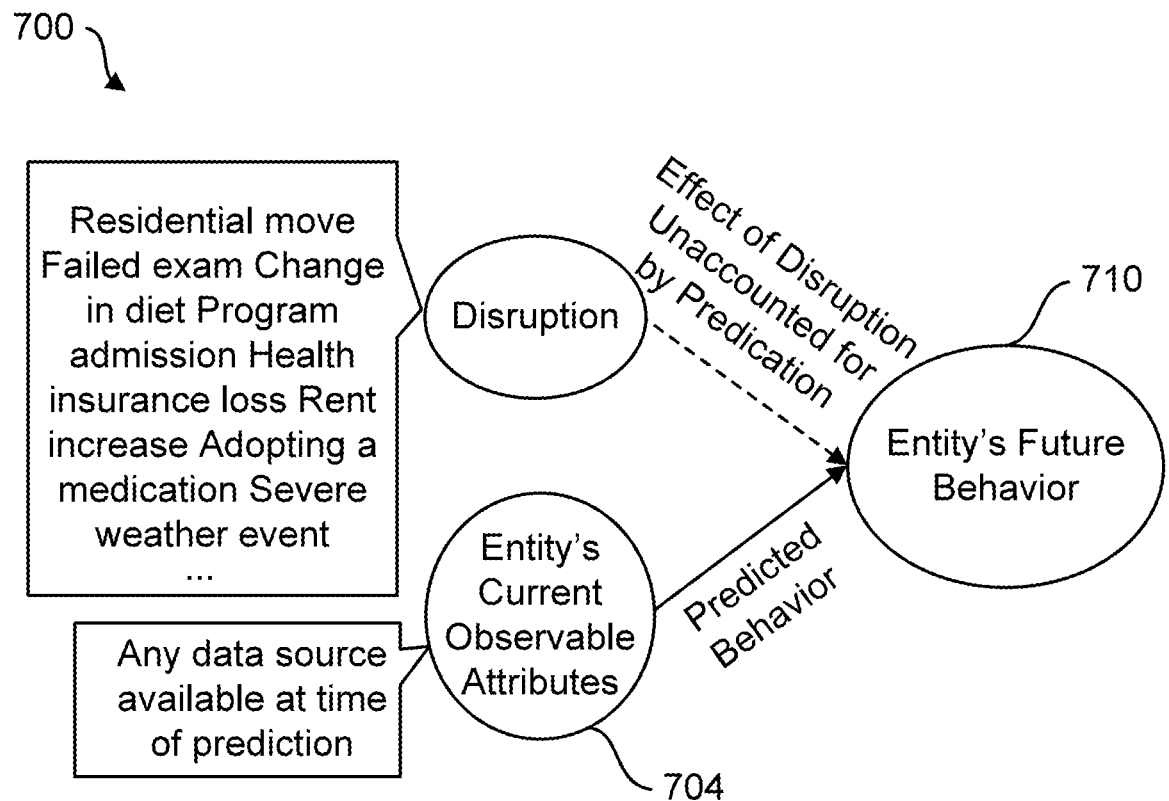
FIG. 7 is a diagram illustrating schematically the interplay of predictions, disruptions, and future entity behavior, in accordance with aspects described herein.

FIG. 7 is a diagram 700 illustrating schematically the interplay of predictions, disruptions, and future entity behavior. As illustrated in FIG. 7, a predictive model may base its prediction 710 of an entity's future behavior on a variety of data sources and data attributes 704 associated with the entity at a certain time. The model may also consider sensitivities to a variety of disruptions 702 to determine an effect of a given disruption to the entity that would otherwise be unaccounted for by the predictive model.

Figure 8:
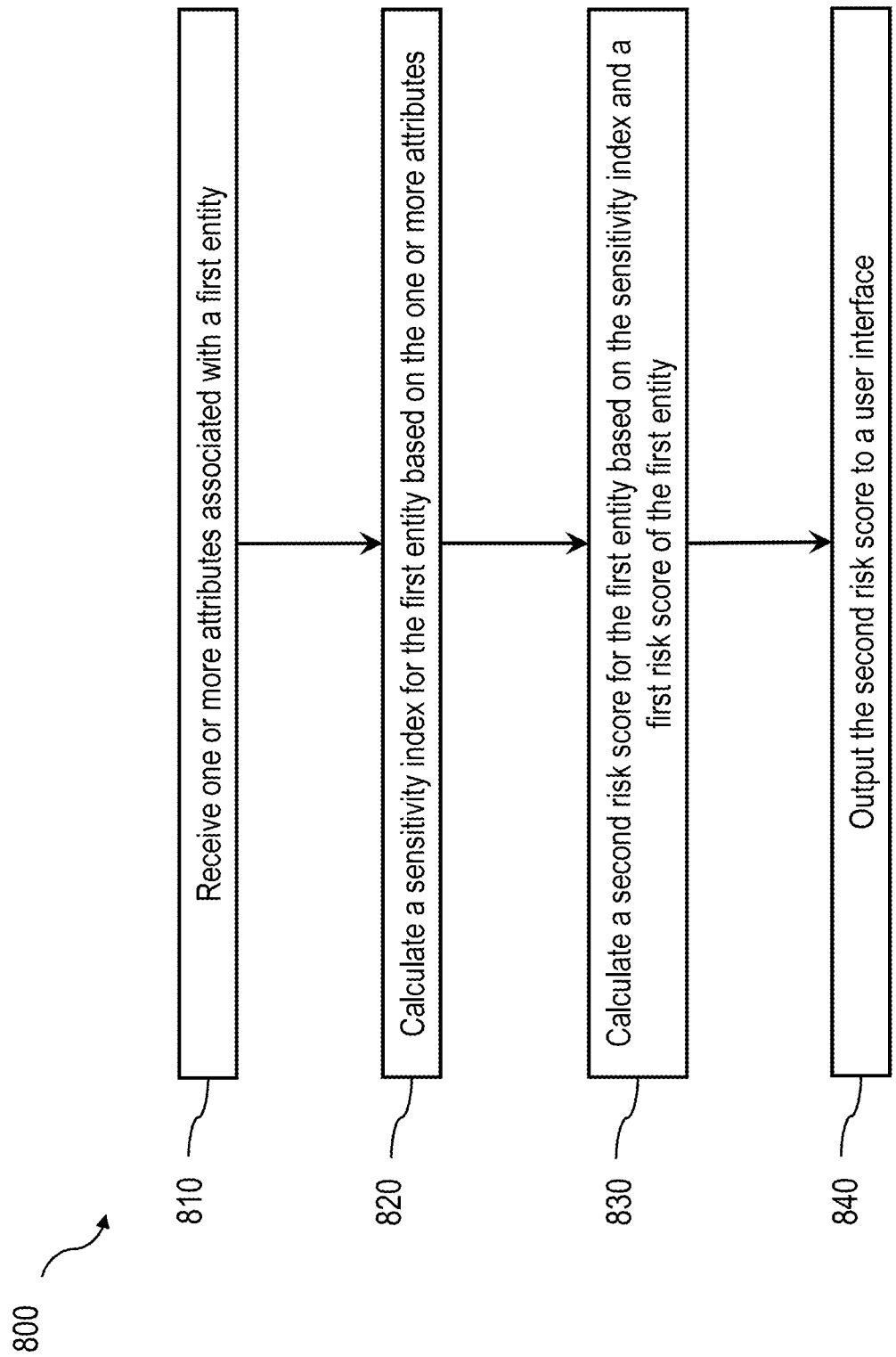
FIG. 8 is a flowchart of a method for segmenting a population based on sensitivities and calculating a sensitivity of predictions about the entity's performance to potential future stressed conditions, in accordance with aspects described herein.

FIG. 8 is a flowchart of a method 800 for segmenting a population based on sensitivities and a calculating risk score based on the segmented sensitivities. In various implementations, the method 800 (or at least a portion thereof) may be performed by the computing system 200, other related apparatuses, and/or some portion thereof. In some aspects, the computing system 200 may be regarded as a server and/or a computer.

Method 800 can start at operational block 810 where the computing system 200, for example, can receive one or more attributes associated with a first entity. Method 800 can proceed to operational block 820 where the computing system 200, for example, can calculate a sensitivity index for the first entity based on the one or more attributes. In some implementations, calculating a sensitivity index can additionally or alternatively involve the computing system 200, for example, creating a matched sample of entities, the entities sharing at least one attribute value of the one or more attributes, the matched sample of entities comprising a first sub-population of the entities experiencing a first condition and a second sub-population of the entities experiencing a second condition, the first sub-population different from the second sub-population. In some implementations, calculating a sensitivity index can additionally or alternatively involve the computing system 200, for example, calculating, for each entity of the matched sample of entities, a sensitivity value associated with the entity, the calculating comprising subtracting an expected performance under the first condition with an expected performance under the second condition. In some implementations, calculating a sensitivity index can additionally or alternatively involve the computing system 200, for example, segmenting, by the computer processor, any sample of entities into two or more segments based on the sensitivity value of each entity, the sensitivity index comprising one of the two or more segments.

Method 800 can proceed to operational block 830 where the computing system 200, for example, can calculate a second risk score for the first entity based on the sensitivity index and the first risk score of the entity. Method 800 can proceed to operational block 830 where the computing system 200, for example, can output the second risk score to a user interface. While the operational blocks of method 800 are illustrated and described in a particular order, each of the operation blocks can be performed in any order.

Certain aspects of the subject matter of the current application are related to features described in co-pending U.S. publication no. 2019/0130481A1, the disclosure of which is incorporated herein by reference in its entirety.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An improved computer-implemented treatment system comprising:
   one or more processors coupled to one or more data storage devices to process or store data associated with known attributes for a plurality of entities subjected to a plurality of known events;
   a machine learning model implemented as a data structure stored in the one or more data storage devices, the machine learning model trained to observe performances of the plurality of entities in a first sub-population and a second sub-population,
   the machine learning model associated with a set of predictors and at least a binary indicator variable corresponding to a first entity subjected to a first event experienced by members of the first sub-population,
   the machine learning model trained to predict an expected performance for the first entity based on at least one of (1) a known attribute associated with the first entity in relation to the first event and (2) a value of the binary indicator variable associated with the first event,
   members of the first sub-population and the second sub-population being distinguishable based on whether one or more events have been experienced by the members of the first sub-population and the second sub-population, the members of the first sub-population experiencing the first event and the members of the second sub-population experiencing a second event,
   wherein an expected performance of the first entity subjected to the first event is determined based on a sensitivity value determined for the first entity by quantifying an expected performance of a member of the first sub-population subjected to the first event according to a sensitivity index generated based on different permutations of potential outcomes for the plurality of known events according to a weighted combination of outputs of multiple sensitivity index models focused on types of disruption or predicted outcomes, the sensitivity index models being generated based on disruption type or target outcome, and
   a treatment being administered to the first entity, responsive to the determined expected performance, wherein the sensitivity index predicts how sensitive a predicted outcome for the first entity is.

2. The system of claim 1, wherein the first sub-population and the second sub-populations optimally capture a binary test of a type of outcome for the sensitivity index based on different events with different time periods associated with different known attributes.

3. The system of claim 2, wherein the different known attributes are contemporaneous to at least one of (1) the different events causing a binary disruption in the first entity's status quo, (2) an absence of the first event, and (3) the second event being less disruptive than the first event.

4. The system of claim 3, wherein the different known attributes have values that are non-randomized, such that the first entity experiencing the first event and a second entity experiencing the second event exhibit materially different distributions of said values.

5. The system of claim 1, wherein the sensitivity index is generated based on at least a first disruption type or a first target outcome.

6. The system of claim 1, wherein a known attribute is determined based on historical data associated with a population of entities having been subjected to an event.

7. The system of claim 4, wherein the population is divided into the first sub-population and the second sub-population based on a propensity score calculated for pairs of matched entities in the population.

8. The system of claim 1, wherein the first event comprises a first medical treatment and the second event comprises a second medical treatment not including the first medical treatment.

9. The system of claim 1, wherein the historical data comprises one or more of age, weight, body mass index, ethnic background, socio-economic factors, and health condition.

10. The system of claim 8, wherein the sensitivity index predicts how sensitive a predicted health outcome for the first entity is depending on a potential future disruption in the first medical treatment.

11. A computer-implemented method executed by one or more processors, the method comprising:
    using one or more processors coupled to one or more data storage devices to process or store data associated with known attributes for a plurality of entities subjected to a plurality of known events,
    a machine learning model implemented as a data structure stored in the one or more data storage devices, the machine learning model trained to observe performances of the plurality of entities in a first sub-population and a second sub-population,
    the machine learning model associated with a set of predictors and at least a binary indicator variable corresponding to a first entity subjected to a first event experience by members of the first sub-population,
    the machine learning model trained to predict an expected performance for the first entity based on at least one of (1) a known attribute associated with the first entity in relation to the first event and (2) a value of the binary indicator variable associated with the first event,
    members of the first sub-population and the second sub-population being distinguishable based on whether one or more events have been experienced by the members of the first sub-population and the second sub-population, the members of the first sub-population experiencing the first event and the members of the second sub-population experiencing a second event, determining, by the one or more processors, an expected performance of the first entity subjected to the first event is determined based on a sensitivity value determined for the first entity by quantifying an expected performance of a member of the first sub-population subjected to the first event according to a sensitivity index generated based on different permutations of potential outcomes for the plurality of known events according to a weighted combination of outputs of multiple sensitivity index models focused on types of disruption or predicted outcomes, the sensitivity index models being generated based on disruption type or target outcome, and administering a treatment to the first entity, responsive to the determined expected performance, wherein the sensitivity index predicts how sensitive a predicted outcome for the first entity is.

12. The method of claim 11, wherein the first sub-population and the second sub-populations optimally capture a binary test of a type of outcome for the sensitivity index based on different events with different time periods associated with different known attributes.

13. The method of claim 12, wherein the different known attributes are contemporaneous to at least one of (1) the different events causing a binary disruption in the first entity's status quo, (2) an absence of the first event, and (3) the second event being less disruptive than the first event.

14. The method of claim 13, wherein the different known attributes have values that are non-randomized, such that the first entity experiencing the first event and a second entity experiencing the second event exhibit materially different distributions of said values.

15. The method of claim 11, wherein the sensitivity index is generated based on at least a first disruption type or a first target outcome.

16. The method of claim 11, wherein a known attribute is determined based on historical data associated with a population of entities having been subjected to an event.

17. The method of claim 16, wherein the population is divided into the first sub-population and the second sub-population based on a propensity score calculated for pairs of matched entities in the population, the first event comprises a first medical treatment and the second event comprises a second medical treatment not including the first medical treatment, the historical data comprises one or more of age, weight, body mass index, ethnic background, socio-economic factors, and health condition, and the sensitivity index predicts how sensitive a predicted health outcome for the first entity is depending on a potential future disruption in the first medical treatment.

18. A non-transitory data storage medium capable of storing instructions that when executed by one or more processors cause a system to:

process or store data associated with known attributes for a plurality of entities subjected to a plurality of known events, a machine learning model implemented as a data structure stored in one or more data storage devices, the machine learning model trained to observe performances of the plurality of entities in a first sub-population and a second sub-population, the machine learning model associated with a set of predictors and at least a binary indicator variable corresponding to a first entity subjected to a first event experience by members of the first sub-population, the machine learning model trained to predict an expected performance for the first entity based on at least one of (1) a known attribute associated with the first entity in relation to the first event and (2) a value of the binary indicator variable associated with the first event, members of the first sub-population and the second sub-population being distinguishable based on whether one or more events have been experienced by the members of the first sub-population and the second sub-population, the members of the first sub-population experiencing the first event and the members of the second sub-population experiencing a second event, determine an expected performance of the first entity subjected to the first event is determined based on a sensitivity value determined for the first entity by quantifying an expected performance of a member of the first sub-population subjected to the first event according to a sensitivity index generated based on different permutations of potential outcomes for the plurality of known events according to a weighted combination of outputs of multiple sensitivity index models focused on types of disruption or predicted outcomes, the sensitivity index models being generated based on disruption type or target outcome, and a treatment being applied to the first entity, responsive to the determined expected performance, wherein the sensitivity index predicts how sensitive a predicted outcome for the first entity is.

19. The data storage medium of claim 18, wherein the first sub-population and the second sub-populations optimally capture a binary test of a type of outcome for the sensitivity index based on different events with different time periods associated with different known attributes and the different known attributes are contemporaneous to at least one of (1) the different events causing a binary disruption in the first entity's status quo, (2) an absence of the first event, and (3) the second event being less disruptive than the first event.

20. The data storage medium of claim 19, wherein the different known attributes have values that are non-randomized, such that the first entity experiencing the first event and a second entity experiencing the second event exhibit materially different distributions of said values, the sensitivity index is generated based on at least a first disruption type or a first target outcome, a known attribute is determined based on historical data associated with a population of entities having been subjected to an event, and the population of entities is divided into the first sub-population and the second sub-population based on a propensity score calculated for pairs of matched entities in the population of entities.

* * * * *